United States Patent
Hamasaki et al.

(10) Patent No.: US 11,058,643 B2
(45) Date of Patent: *Jul. 13, 2021

(54) COMPOSITION FOR OUTER LAYER OF SOLID PREPARATION, AND EASY-TO-TAKE SOLID PREPARATION INCLUDING SAID COMPOSITION FOR OUTER LAYER

(71) Applicant: DAICEL CORPORATION, Osaka (JP)

(72) Inventors: Momoko Hamasaki, Himeji (JP); Tomohito Okabayashi, Himeji (JP); Anan Sakaguchi, Himeji (JP); Atsuhiro Uetomo, Himeji (JP); Takahiro Hiramura, Tokyo (JP)

(73) Assignee: DAICEL CORPORATION, Osaka (JP)

( * ) Notice: Subject to any disclaimer, the term of this patent is extended or adjusted under 35 U.S.C. 154(b) by 41 days.

This patent is subject to a terminal disclaimer.

(21) Appl. No.: 15/739,202

(22) PCT Filed: Jun. 28, 2016

(86) PCT No.: PCT/JP2016/069132
§ 371 (c)(1),
(2) Date: Apr. 24, 2018

(87) PCT Pub. No.: WO2017/002803
PCT Pub. Date: Jan. 5, 2017

(65) Prior Publication Data
US 2018/0243221 A1 Aug. 30, 2018

(30) Foreign Application Priority Data
Jun. 29, 2015 (JP) .............................. JP2015-129531

(51) Int. Cl.
*A61K 9/20* (2006.01)
*A61K 9/16* (2006.01)
*A61K 47/36* (2006.01)
*A61K 47/38* (2006.01)
*A61K 47/10* (2017.01)

(52) U.S. Cl.
CPC .............. *A61K 9/2054* (2013.01); *A61K 9/16* (2013.01); *A61K 9/20* (2013.01); *A61K 9/2018* (2013.01); *A61K 9/2095* (2013.01); *A61K 47/10* (2013.01); *A61K 47/36* (2013.01); *A61K 47/38* (2013.01)

(58) Field of Classification Search
CPC .. A61K 9/2054; A61K 9/2095; A61K 9/2018; A61K 9/20; A61K 9/16; A61K 47/38; A61K 47/36; A61K 47/10; A61K 9/205; A61K 9/1652; A61K 9/1623; A61K 19/20
See application file for complete search history.

(56) References Cited

U.S. PATENT DOCUMENTS

| | | | | |
|---|---|---|---|---|
| 5,667,573 A | * | 9/1997 | Kondou ................. | A23G 3/343 106/194.2 |
| 10,292,934 B2 | * | 5/2019 | Hiramura ............. | A61K 9/0056 |
| 2005/0202082 A1 | * | 9/2005 | Hibino ...................... | A61J 3/10 424/464 |
| 2015/0225590 A1 | * | 8/2015 | Iotti ......................... | C08K 5/17 428/535 |
| 2015/0238424 A1 | * | 8/2015 | Hiramura ............. | A61K 9/0056 514/772.1 |
| 2016/0088869 A1 | * | 3/2016 | Haggblom ............ | A23L 3/3562 426/103 |

FOREIGN PATENT DOCUMENTS

| | | | | |
|---|---|---|---|---|
| EP | 2 561 892 | | 2/2013 | |
| JP | 2000516222 | | 12/2000 | |
| JP | 2010260803 | * | 8/2010 | |
| JP | 5433295 | | 3/2014 | |
| JP | WO2014046035 | * | 3/2014 | |
| JP | 2015096490 | | 5/2015 | |
| WO | WO-2006062089 A1 | * | 6/2006 | ............... C08L 1/02 |
| WO | 2014046035 | | 3/2014 | |
| WO | 2015163135 | | 10/2015 | |

OTHER PUBLICATIONS

Supplementary European Search Report of Application No. EP 16817911 dated Jan. 28, 2019.
Kolakovic, R. et al., "Spray-dried cellulose nanofibers as novel tablet excipient", AAPS Pharm. Sci. Tech., 2011, vol. 12(4), pp. 1366-1373.
International Search Report of International Application No. PCT/JP2016/069132 dated Aug. 2, 2016.

* cited by examiner

*Primary Examiner* — Snigdha Maewall
(74) *Attorney, Agent, or Firm* — Ping Wang; Morris, Manning & Martin LLP

(57) ABSTRACT

The purpose of present invention to provide a particulate composition that has the excellent provides moldability and useful as a composition that is used as an outer layer of a solid preparation, especially an easy-to-take solid preparation and the like; a composition for an easy-to-take solid preparation, which comprises the particulate composition and a gelling agent that will show slipperiness when it is brought into contact with water; and a solid preparation comprising the composition.
The present invention relates to a particulate composition comprising sugar alcohol and a water-insoluble polymer; a composition for an easy-to-take solid preparation, which comprises the particulate composition and a gelling agent that will show slipperiness when it is brought into contact with water; and a solid preparation comprising the composition and the like.

12 Claims, No Drawings

COMPOSITION FOR OUTER LAYER OF SOLID PREPARATION, AND EASY-TO-TAKE SOLID PREPARATION INCLUDING SAID COMPOSITION FOR OUTER LAYER

TECHNICAL FIELD

The present invention relates to a particulate composition comprising sugar alcohol and a water-insoluble polymer; to a composition for an outer layer (the composition that is used as an outer layer) of an easy-to-take solid preparation and the like, which comprises the particulate composition and a gelling agent that will show slipperiness when it is brought into contact with water; and to a solid preparation comprising the composition; for the outer layer and the like.

BACKGROUND ART

Taking properties of a preparation for oral administration have been previously improved for patients who have difficulty in swallowing, elderly people and children who have a weak swallowing ability and the like. For example, the preparations are formulated into liquid or jelly preparation form in many cases. However, when a content of a main drug is high, it will be difficult to mask its taste. And, when an active ingredient such as a drug is unstable in water, it will be difficult to be formulated in any preparation form.

Accordingly, easy-to-take preparations have been recently developed for facilitating swallowing of the solid preparation, wherein the surface of the preparations is coated, with a gelling agent so that they will show slipperiness and become slippery against mucous membrane and easy to swallow when they are brought into contact with water in oral cavity.

These techniques use processes such as, for example, 1) formulating gell into a tablet by freeze-drying of; 2) punching into a circle shape a film of gelling layers comprising a drug layer between them; 3) punching into a circle shape gelling film layers comprising a tablet between them; 4) spraying a coating solution for gelling on a tablet, and the like.

Patent Literature (PTL) 1 discloses a coating composition for use in an easy-to-take solid, preparation, which comprises a first, thickener of a metal-crosslinking thickener, a polyvalent metal compound, and a second thickener; a method for the production of a preparation for oral administration by spray-coating alcohol solution having the coating composition dispersed therein onto a drug core comprising an active ingredient; and the preparation for oral administration produced thereby.

Patent Literature (PTL) 2 discloses a method for molding a product having a core by using a molding material such as particulate as a starting material, and a rotary-type nucleated-tabletting machine (compression molding means.

Patent Literature (PTL) 3 discloses 100% erythritol spherical particulate for a direct compression, which is obtained by granulating under spraying of ethanol, drying and grading 100% erythritol ultra-fine powder in a range of from 0.4 μm to 23 μm of an average diameter for the purpose of providing the 100% erythritol spherical particulate.

Patent Literature (PTL) 4 discloses a method for the production of an excipient for use in compression processing for foods and pharmaceuticals, which comprises spraying and granulating aqueous solution of sugar alcohol by means of a fluidized-bed granulation coating device to obtain assembly of granulated sugar alcohol without formulating a binder.

However, none of these patent documents discloses the particulate composition comprising the sugar alcohol and the water-insoluble polymer; the composition for the outer layer of the easy-to-take solid preparation and the like, which comprises the particulate composition and the gelling agent that will show slipperiness when it is brought into contact with water; or the solid preparation comprising the composition for the outer layer and the like.

RELATED ARTS

Patent Literatures

PTL 1: International Publication Pamphlet WO2011/125798
PTL 2: Japanese Patent Application Publication Hei 2 (1990)-38079
PTL 3: JP-A-2014-210746
PTL 4: Japanese Patent No. 3491887
PTL 5: JP-A-Sho56 (1981)-100801
PTL 6: JP-A-2009-203559

SUMMARY OF INVENTION

Problems to be Solved by the Invention

The conventional treatment with a gelling agent seen in the prior arts such as PTL 1 was complicated since it requires the preparation of a gelling agent solution, the transfer to a coating machine after the compression molding and the like. Furthermore, a functional or active ingredient cannot be used if their stability for a solvent used in these processes is low. There has been a problem that it was difficult to form a thick coating layer when the gelling agent was coated.

Granulation of the erythritol spherical particulate for direct compression of PTL 3 will need an organic solvent, and it will also require the addition of other additives in order to obtain a desired, tablet hardness since formability of the resulting particulate is low. The method disclosed in PTL 4 has problems such as that the granulating conditions need to be controlled strictly and that a rotary container is required since a usual fluidized-bed granulation would generate aggregation and fixing of the sugar alcohol.

Accordingly, an object of the present invention is to solve such technical problems in the arts, and to provide a particulate composition that has excellent moldability and useful for the solid preparation; a composition for the easy-to-take solid preparation, which comprises the particulate composition and the gelling agent that will show slipperiness when it is brought into contact with water; and the solid preparation comprising the composition. The term "easy-to-take" generally means "easy to drink" or "easy to swallow", as the characteristics or property of the solid preparations and the like.

Another object of the present invention is to provide a method for the production of the easy-to-take solid preparation, comprising only a step of compression-molding the composition in a dry process.

Neither of the above Patent Literatures discloses or suggests such technical problems.

Means to Solve the Problem

The present inventors have earnestly studied to solve the above problems and completed the invention comprising the following aspects Thus, the present invention provides the following aspects.

[Aspect 1]

A particulate composition comprising sugar alcohol and a water-insoluble polymer.

[Aspect 2]

The particulate composition according to Aspect 1, wherein the water-insoluble polymer is micro-fibrillated cellulose.

[Aspect 3]

The particulate composition according to Aspect 2, wherein the micro-fibrillated cellulose has an average fiber length of 0.01-2 mm, and an average fiber diameter of 0.001-1 μm.

[Aspect 4]

The particulate composition according to Aspect 1, wherein the water-insoluble polymer is crystalline cellulose.

[Aspect 5]

The particulate composition according to any one of Aspects 1-4, wherein the sugar alcohol comprises one or more selected from the group consisting of erythritol, xylitol, mannitol, sorbitol, lactitol, isomalt and maltitol.

[Aspect 6]

A composition for an easy-to-take solid preparation, which comprises the particulate composition according to any one of Aspects 1-5 and a gelling agent that will show slipperiness when it is brought into contact with water.

[Aspect 7]

The composition according to Aspect 6, wherein the gelling agent comprises at least one kind of a water-soluble polymer.

[Aspect 8]

The composition according to Aspect 7, wherein the water-soluble polymer is selected from the group consisting of sodium carmellose, xanthan gum, sodium alginate, carrageenan and gelatin.

[Aspect 9]

The composition according to Aspect 6, comprising sodium carmellose, erythritol or xylitol, and the micro-fibrillated cellulose.

[Aspect 10]

The composition according to any one of Aspects 6-9, which is used, as an outer layer of the easy-to-take solid preparation.

[Aspect 11]

A solid preparation comprising the particulate composition according to Aspects 1-5.

[Aspect 12]

An easy-to-take solid preparation comprising the composition according to Aspects 6-10.

[Aspect 13]

The easy-to-take solid preparation according to Aspect 12, which is in a form of granule for foods or pharmaceuticals.

[Aspect 14]

An easy-to-take solid preparation for foods or pharmaceuticals, wherein an inner core is coated with the composition that is used as the outer layer according to Aspect 10.

[Aspect 15]

A method for the production of the easy-to-take solid preparation according to any one of Aspects 12-14, comprising only a step of compression-molding the composition in a dry process.

Advantages of Invention

The present invention provides the particulate composition that has the excellent moldability and useful as the composition for an outer layer of the solid preparation, especially the easy-to-take solid preparation and the like, so that the intercalation between an inner layer (inner core) and the outer layer of the solid preparation can be inhibited. Furthermore, the present invention makes it possible to increase thickness of the outer layer of the preparation so as to increase easiness to swallow, and increase a masking effect for the taste of a core tablet.

Furthermore, since it is possible to produce the easy-to-take solid preparation without going through any wet condition, functional or active ingredients can be used even if their stability for a solvent is low.

EMBODIMENTS FOR CARRYING OUT THE INVENTION

A first aspect of the present invention relates to the particulate composition comprising the sugar alcohol and the water-insoluble polymer. As shown by the Examples in the present specification, the above particulate composition has the excellent moldability.

Any material known for those skilled in the art may be used as the water-insoluble polymer as long as it can effectively improve the moldability of the composition. It may be naturally-occurring or synthetic one.

Preferable examples of the water-insoluble polymer include micro-fibrillated cellulose, crystalline cellulose, powdered cellulose and various kinds of cellulose derivatives. The micro-fibrillated cellulose is most preferred among them.

The micro-fibrillated cellulose is generally produced from the vegetable fiber and having the fiber diameter (the short diameter) or thickness of from about a few nm to 1 μm. The surface area of the micro-fibrillated cellulose has been increased, its hydrophilic property that is the original characteristics of cellulose has been significantly strengthened, and its three-dimensional network has been formed, without deteriorating the basic properties such physical and chemical stabilities of the starting material of cellulose.

A dry material of the micro-fibrillated cellulose may be directly obtained in a dry state by any method known in the art, such as by directly pulverizing cellulose fiber in a dry state with a ball mill (PTL 5). Alternatively, the dry material of the micro-fibrillated cellulose may be obtained by subjecting the micro-fibrillated cellulose suspended in water, which was prepared by micro-fibrillation of water-dispersion of the cellulose fiber with a high-pressure homogenizer, to a solvent displacement stage, and removing the solvent in a drying stage, followed by pulverization in a pulverizing stage (PTL 6).

Preferable examples of the micro-fibrillated cellulose include fiber assembly that has an average fiber length of 0.01~2 mm and an average fiber diameter of 0.001~1 μm, preferably of 0.01~0.1 μm (PTL 2). For example, such micro-fibrillated cellulose is commercially available with a trade name of "CELISH" series (a solid content of 10~35% in water) with various grades (an average fiber diameter of 0.01~0.1 μm) from Daicel FineChem Ltd.

Representative examples of the crystalline cellulose include commercially-available products such as "Avicel" (FMC Corporation), "CEOLUS" (Asahi Kasei Chemicals Corp.), and "VIVAPUR" (RETTENMAIER) can be mentioned. Representative examples of the powdered cellulose include KC Flock (NIPPON PAPER Chemicals CO., LTD) and ARBOCEL (RETTENMAIER) and Solka Flock (Kimura Sangyo Co., Ltd.) and the like.

The sugar alcohol may be any one known for those skilled in the art such as one or more selected from the group consisting of erythritol, xylitol, mannitol, sorbitol, lactitol, isomalt and maltitol.

Although a mixing ratio of the sugar alcohol and the water-insoluble polymer may be optionally determined by those skilled in the art, preferably, it is usually in a range of from 99:1 to 80:20 by weight. The particulate composition may be produced by any method or means known in the art, for example, by spraying a suspension of the water-insoluble polymer onto the sugar alcohol as described in the Examples.

It is preferable that the particulate composition of the present invention has the following physical properties:
(1) an average particle size of 50 to 500 microns; and
(2) a water content of 0.1% to 2.0% by weight.

A second aspect, of the present invention relates to the composition for the easy-to-take solid preparation, which comprises the particulate composition according to the present invention and the gelling agent that will show slipperiness when it is brought into contact with water, for example, to the composition for the outer layer (or, the composition that is used as the outer layer) of the easy-to-take solid preparation. The above composition has an excellent moldability as well, as shown by the Examples in the present specification.

The gelling agent that will show slipperiness when it is brought into contact with water according to the present invention means a material that will form a slippery surface of a solid tablet under the moisture condition in the oral cavity when it is taken without water so as to promote the slipperiness of the tablet itself. Such promotion of the slipperiness of the tablet will also make the tablet easy to swallow even when it is taken with water.

The representative examples of the gelling agent include the water-soluble polymer that is selected from the group consisting of sodium carboxymethylcellulose (also, called "sodium carmellose"), sodium alginate, carrageenan, xanthan gum and gelatin. The water-soluble polymer may be naturally-occurring or synthetic one.

A preferable example of the composition comprises sodium carmellose, erythritol or xylitol, and the microfibrillated cellulose. Although a mixing ratio of the particulate composition and the gelling agent that will show slipperiness when it is brought into contact with water may be optionally determined by those skilled in the art, preferably, it is usually in a range of from 10:90 to 99:1 by weight. Other components may be comprised in the composition. The composition may be produced by any method or means known in the art as described in the Examples.

A third aspect of the present invention relates to the solid preparation comprising the particulate composition according to the present invention. The particulate composition may be comprised in the solid preparation as any constituent or in any form. Examples of the solid preparation include the easy-to-take solid preparation that comprises the composition according to the second aspect of the present invention as, for example, the composition for its outer layer.

A preferable example of the easy-to-take solid preparation may be the easy-to-take solid preparation for foods or pharmaceuticals, wherein the inner core is coated with the above composition for the outer layer, or granule for foods or pharmaceuticals, comprising the composition for the easy-to-take solid preparation according to the present invention.

The easy-to-take solid preparation according to the present invention may be produced by any means or method known for those skilled in the art, especially by the production method described below.

Thus, there may be listed a dry-process method for the production of an easy-to-take solid preparation wherein an inner core tablet is coated with a compression-molded outer layer-forming agent (an outer layer) comprising a gelling agent that will show slipperiness when it is brought into contact with water, comprising loading separately or simultaneously the inner core tablet and powder of the composition for the outer layer to a mortar inner surface, the bottom end surface of an upper-pestle, and the top end surface of a lower-pestle, and subsequently compression-molding them. The inner core tablet may be prepared using a core-molding material by any means or method known for those skilled in the art, preferably being obtained by compression-molding the core-molding material in the dry process. The inner core tablet and the powder of the composition for the outer layer may be loaded after a lubricant has been applied to the mortar inner surface, and the surfaces of the upper-pestle and the lower-pestle.

The "powder" in the above method means the aggregate of solid particulates, which may include powder having finer size or shape than granules or grains. The ingredients comprised in the powder of the composition for the outer layer and the core-molding material may be used as they are, or the powder of the outer layer-forming agent and the core-molding material may be prepared by any means or method known in the art such as a dry granulation process, a wet granulation process and the like.

The dry granulation process includes crushing granulation and roll-compressing method, comprising the steps of compressing each powder components into small bulks with a pressure, and appropriately crushing and granulating them, for example.

On the other hand, the wet granulation process is a method in which each component is dispersed in the presence of water, and the dispersion is dried to form complexes. As specific examples of the wet granulation process, spray methods such as spray drying, tumbling granulation, agitation granulation and fluidized-bed granulation; freeze-drying method; kneading granulation, and the like can be mentioned. They can be produced by any of these methods known to a person skilled in the art.

In the method according to the present invention, the mortar, the upper-pestle, and the lower-pestle are a member for compressing the inner core tablet and the outer layer-forming agent along the four directions, so as to mold the easy-to-take solid preparation wherein the inner core tablet is coated with the compression-molded composition for the outer layer. They comprise any other members that are named differently in any other powder compression-molding machines or devices as long as they have substantially the same functions and/or properties as the above ones.

Each process of loading the inner core tablet and the powder of the composition for the outer layer to the mortar inner surface, the bottom end surface of the upper-pestle, and the top end surface of the lower-pestle, etc. may be performed by any means or method known for those skilled in the art depending on the production machine used and the like. For example, the loading of the inner core tablet and the powder of the composition for the outer layer to the mortar inner surface, the bottom end surface of the upper-pestle, and the top end surface of the lower-pestle may be simultaneously or separately carried out by using any appropriate means, or the powder of the composition for the outer layer may be loaded repeatedly a few times. For example, the powder of the composition for the outer layer is loaded, followed by the loading of the inner core tablet, and then followed by the loading of the powder of the composition for the outer layer again. Furthermore, compression-molding of the inner core tablet and the powder of the composition for the outer layer may be carried out all at once.

The solid preparation, especially, the easy-to-take solid preparation according to the present invention is an oral formulation that is called a "nucleated tablet" as well, and has uses, for example, as various foods such as supplemental foods, nutrition function foods and health foods; and as pharmaceuticals.

The core-molding material in the above method may therefore optionally comprise various components known for those skilled in the art depending on the above uses.

For use as the foods, for example, it may comprise various nutritional components such, as proteins, carbohydrates, lipids and minerals; components for health foods such as various extracts from microorganisms, plants and animals; various vitamins and their derivatives; and designated or existing additives according to Food Sanitation Law, Art. 10; and other components acceptable as a food component, (a food additive) listed in a list of general additives for food and drink, such as acidulants, sweeteners, excipients, surfactants, lubricants, auxiliary agents, corrigents, flavoring agents, colorants, and stabilizing agents.

For use as the pharmaceuticals, for example, it may comprise in addition to a medicinal or active ingredient, other any pharmaceutically acceptable components, such as excipients, surfactants, lubricants, auxiliary agents, acidulants, sweeteners, corrigents, flavoring agents, colorants, and stabilizing agents, when needed. As these optional components, for example, appropriate ingredients described in "Japanese Pharmaceutical Excipients Directory" (YAKUJI NIPPO LIMITED) or the Japanese Pharmacopoeia; designated or existing additives according to Food Sanitation Law, Art. 10; natural flavor; and additives listed in a list of general additives for food and drink can be used. There is no limitation in the kind of the medicinal ingredient and the above auxiliaries. Also, the blending ratios of each optional ingredient (component) are not particularly limited as long as the desired effects of the present invention are brought about, and the blending ratios can properly be determined by those skilled in the art.

There is no limitation on an application or kind of the medicinal ingredients, which may include, for example, agents affecting each organ such as the central, nervous system, peripheral nervous system, a sensory organ, a circulatory organ, a respiratory organ and a digestive organ and an urogenital organ; hormone drug; agents affecting metabolism such as a vitamin drug, an analeptic, an agent affecting blood and body fluid; agents affecting the function of tissue and cell such, as an agent activating cellular function, an agent affecting tumors, an radioactive medicine, an anti-allergic agent; medicines based on a medical prescription relating to herbal medicines and Chinese medicines; antibiotics; agents for chemotherapy, biological drug; agents for pathogenic organisms such as parasites; agents for formulation use, diagnosis, public health and in-vitro diagnosis.

Those skilled in the art may optionally select the various conditions in the processes of the production method according to the present invention, such as pressure and time of the compression-molding, and amounts of the composition for the outer layer and the core-molding material, depending on the scale and kind of the machine to be used in the method, the size and application of a desired easy-to-take solid preparation and the like. For example, tablet compression force in the compression-molding usually ranges from 2 to 100 kN.

There is no limitation on the size, shape and the like of the solid preparation according to the present invention. It is usually within a range of from 3 to 20 mm in diameter and of from 15 to 2000 mg in weight. And, the inner core tablet usually has a diameter with a range of from 1.8 to 18 mm and a weight with a range of from 10 to 1800 mg. They may have any shape known for those skilled in the art such as those of a flat with bevel-edge tablet and a truly-flat tablet. The thickness of the outer layer (coating) consisting of the composition for the outer layer ranges from about 0.1 to about 5 mm. These values can be determined by any method known for those skilled in the art.

In addition, contents of all related art documents cited in the present specification are incorporated herein by reference.

Hereinafter, the present invention will more specifically be described with reference to Examples. However, the present invention is not considered to be limited to the Examples.

[Evaluation on Average Diameter of the Particulate, Water Content, Hardness, Thickness of the Outer Layer, Slipperiness, Easiness to Peel Off, and Taste-Masking Effect]

The tablets obtained in the Examples and Comparative Example were measured based on the following conditions/methods with respect to an average diameter of the particulate, water content, hardness, thickness of the outer layer, slipperiness, easiness to peel off the outer layer, and taste-masking effect.

Average particle diameter: 2 g of the disintegrative particulate composition is subjected to a measurement with a Φ75 mm automatic shaking sieve device (Type "M-2", Tsutsui Scientific Instruments Co., Ltd.).

Water content: 5 g of the disintegrative particulate composition is subjected to a measurement using a halogen water content measuring device (Type "HB43", METTLER TOLEDO K.K.).

Hardness; Hardness (N) was measured with a digital Kiya hardness tester (Fujiwara Scientific Company Co., Ltd.). The measurement for the hardness was repeated six times for each tablet, and an average value thereof was regarded as a measurement result.

Thickness of the outer layer: The tablet was fractured and thickness of the resulting cross section was measured with a loupe equipped with ×10 scale (0.1 mm per scale). An average value was regarded as a measurement result. In case where it was hard to distinguish the outer layer from the inner core tablet, an edible dye was added in advance into the inner core tablet, and the thickness of the outer layer was measured.

Slipperiness: Three men and women, respectively took the tablet without water, and slipperiness was evaluated in accordance with four-stage criteria below:

4: slipperiness is maintained and very easy to swallow

3: slippery and easy to swallow

2: slightly slippery but hard to swallow

1: hardly slippery and hard to swallow

Easiness to peel off: After five tablets had been kept for one week in a PE bag, the number of the tablets whose surface was peeled off when taken by hands was counted.

Taste-masking effect: Five men and women, respectively took the tablet without water, and an average time during which the taste of the core tablet could not be felt was regarded as a measurement result.

Example 1

[Production of the Particulate Composition 1]

368 g of erythritol (Erythritol T, Mitsubishi-Chemical Foods Corporation) was charged to a fluidized-bed granulator (FL-LABO, Freund Corporation), and 640 g of 5% suspension of wet material of micro-fibrillated cellulose ("CELISH", Daicel FineChem Ltd.) in water was sprayed onto it at a rate of 12 g/minute for granulation to thereby obtain particulate composition 1 according to the present invention. The resulting particulate composition 1 had the following values for physical properties: (1) an average particle size of 171 microns and (2) a water content of 0.40% by weight.

[Evaluation of the Particulate Composition 1]

The resulting particulate composition 1 was then subjected to tableting at a tablet compression force of 8 kN with a simple tableting machine (HANDTAB-100, ICHIHASHI-SEIKI Co., Ltd.) to thereby obtain a flat with bevel-edge tablet having a diameter of 8.0 mm and a weight of 250 mg.

Example 2

[Production of the Particulate Composition 2]

384 g of pulverized xylitol product (Xylite, Mitsubishi-Chemical Foods Corporation) was charged to the fluidized-bed granulator (FL-LABO, Freund Corporation), and 320 g of 5% suspension of wet material of micro-fibrillated cellulose ("CELISH", Daicel FineChem Ltd.) in water was sprayed onto it at a rate of 12 g/minute for granulation to thereby obtain particulate composition 2 according to the present invention. The resulting particulate composition 2 had the following values for physical properties: (1) an average particle size of 295 microns and (2) a water content of 0.28% by weight.

[Evaluation of the Particulate Composition 2]

The resulting particulate composition 2 was then subjected to tableting in the same way as in Example 1 to thereby obtain a flat with bevel-edge tablet having a diameter of 8.0 mm and a weight of 250 mg.

Example 3

[Production of the Particulate Composition 3]

380 g of pulverized xylitol product (Xylite, Mitsubishi-Chemical Foods Corporation) and 20 g of crystalline cellulose (CEOLUS Asahi Kasei Chemicals Corp.) were charged to the fluidized-bed granulator (FL-LABO, Freund Corporation), and 320 g of water was sprayed onto them at a rate of 12 g/minute for granulation to thereby obtain particulate composition 3 according to the present invention. The resulting particulate composition 3 had the following values for physical properties: (1) an average particle size of 207 microns and (2) a water content of 0.50% by weight.

[Evaluation of the Particulate Composition 3]

The resulting particulate composition 3 was then subjected to tableting in the same way as in Example 1 to thereby obtain a flat with bevel-edge tablet having a diameter of 8.0 ram and a weight of 250 mg.

Example 4

[Production of the Particulate Composition 4]

384 g of pulverized maltitol fine powder product (LESYS, Mitsubishi-Chemical Foods Corporation) was charged to the fluidized-bed granulator (FL-LABO, Freund Corporation), and 320 g of 5% suspension of wet material of micro-fibrillated cellulose ("CELISH", Daicel FineChem Ltd.) in water was sprayed onto it at a rate of 12 g/minute for granulation to thereby obtain particulate composition 4 according to the present invention. The resulting particulate composition 4 had the following values for physical properties: (1) an average particle size of 251 microns and (2) a water content of 0.62% by weight.

[Evaluation of the Particulate Composition 4]

The resulting particulate composition 4 was then subjected to tableting in the same way as in Example 1 to thereby obtain a flat with bevel-edge tablet having a diameter of 8.0 mm and a weight of 250 mg.

Comparative Example 1

304 g of erythritol (Erythritol T, Mitsubishi-Chemical Foods Corporation) was charged to the fluidized-bed granulator (FL-LABO, Freund Corporation), and 320 q of 30% aqueous solution, of erythritol was sprayed onto it at a rate of 12 g/minute for granulation to thereby obtain particulate composition. The resulting particulate composition had the following values for physical properties: (1) an average particle size of 452 microns and (2) a water content of 1.64% by weight.

The resulting particulate composition was then subjected to tableting in the same way as in Example 1 to thereby obtain a flat with bevel-edge tablet having a diameter of 8.0 mm and a weight of 250 mg.

[Evaluation of Hardness]

Tablet Hardness of each tablet produced in the above Examples and Comparative Examples are shown in Table 1.

TABLE 1

| | Ex. 1 | Ex. 2 | Ex. 3 | Ex. 4 | Comp. Ex. 1 |
| --- | --- | --- | --- | --- | --- |
| Tablet Compression Force (kN) | 8 | 8 | 8 | 8 | 8 |
| Tablet Hardness (N) | 95 | 103 | 103 | 200 | 16 |

The results shown in Table 1 demonstrate that the tablets obtained with the particulate composition produced by the methods comprising the wet granulation process using the micro-fibrillated slurry in Examples 1, 2 and 4, and by the methods comprising the wet granulation process with the addition of crystalline cellulose in Example 3 had such an excellent moldability as to give a high tablet hardness, when compared to the tablet obtained with the particulate composition (Comparative Example 1) produced by the methods comprising the granulation process using only sugar alcohols.

Example 5

4.0 g of the particulate composition obtained in Example 1 and 1.0 g of sodium carmellose (CMC Daicel, Daicel FineChem Ltd.) were mixed to obtain the composition according to the present invention. The resulting composition was then subjected to tableting at a tablet compression force of 8 kN with the simple tableting machine (HANDTAB-100, ICHIHASHI-SEIKI Co., Ltd.) to thereby obtain a flat with bevel-edge tablet having a diameter of 8.0 mm and a weight of 250 mg, wherein a small amount of calcium stearate (Taihei Chemical Industrial Co. Ltd.) had been applied in advance to a mortar inner surface, and the surfaces of an upper-pestle and a lower-pestle in the above tableting machine.

Example 6

4.0 g of the particulate composition obtained in Example 2 and 1.0 g of sodium carmellose (CMC Daicel, Daicel FineChem Ltd.) were mixed to obtain the composition according to the present invention. The resulting composition was then subjected to tableting in the same way as in Example 5 to thereby obtain a flat with bevel-edge tablet having a diameter of 8.0 mm and a weight of 250 mg.

Example 7

4.0 g of the particulate composition obtained in Example 4 and 1.0 g of sodium carmellose (CMC Daicel, Daicel FineChem Ltd.) were mixed to obtain the composition according to the present invention. The resulting composition was then subjected to tableting in the same way as in Example 5 to thereby obtain a flat with bevel-edge tablet having a diameter of 8.0 mm and a weight of 250 mg.

Comparative Example 2

4.0 g of erythritol (Erythritol T fine powder, Mitsubishi-Chemical Foods Corporation) and 1.0 g of sodium carmellose (CMC Daicel, Daicel FineChem Ltd.) were mixed, and then subjected to tableting in the same way as in Example 5 except for at a tablet compression force of 14 kN to thereby obtain a flat with bevel-edge tablet having a diameter of 8.0 mm and a weight of 250 mg.

Comparative Example 3

4.0 g of xylitol (Xylite fine powder, Mitsubishi-Chemical Foods Corporation) and 1.0 g of sodium carmellose (CMC Daicel, Daicel FineChem Ltd.) were mixed, and then subjected to tableting in the same way as in Comparative Example 2 to thereby obtain a flat with bevel-edge tablet having a diameter of 8.0 mm and a weight of 250 mg.

Comparative Example 4

3.5 g of erythritol (Erythritol T fine powder, Mitsubishi-Chemical Foods Corporation), 1.0 g of sodium carmellose (CMC Daicel, Daicel FineChem Ltd.) and 0.5 g of crystalline cellulose (CEOLOS Asahi Kasei Chemicals Corp.) were mixed, and then subjected to tableting in the same way as in Comparative Example 2 to thereby obtain a flat with bevel-edge tablet having a diameter of 8.0 mm and a weight of 250 mg.

[Evaluation of Hardness]

Tablet Hardness of each tablet produced in Examples 5-7, and Comparative Examples 2 and 3 are shown in Table 2.

TABLE 2

|  | Ex. 5 | Ex. 6 | Ex. 7 | Comp. Ex. 2 | Comp. Ex. 3 |
|---|---|---|---|---|---|
| Tablet Compression Force (kN) | 8 | 8 | 8 | 14 | 14 |
| Tablet Hardness (N) | 65 | 58 | 130 | 16 | 16 |

The results shown in Table 2 demonstrate that the tablets obtained by using the composition comprising the sugar alcohol granulated with spraying of the water-insoluble polymer (the particulate composition) and the water-soluble polymer in Examples 5-7 had such an excellent moldability as to give a high tablet hardness even under a low tablet compression force, when compared to the tablet obtained by using the mixture of the sugar alcohol and the water-soluble polymer in Comparative Examples 2 and 3.

The tablet obtained by using the mixture comprising the crystalline cellulose in addition to the sugar alcohol and the water-soluble polymer in Comparative Example 4 showed such an improved moldability as a tablet hardness of 23 N at a tablet compression force of 8 kN due to the addition of the crystalline cellulose, when compared to the tablet produced in Comparative Example 2. However, the resulting moldability was not sufficient. Besides, in the case where the composition according to the present invention is used as the outer layer of the easy-to-take solid preparation, the higher a content of the cellulose in the outer layer become, the higher an amount of water absorbed by cellulose, so that it will take more time to exhibit slippery property, and need more water. It is therefore not preferred to increase the amount of cellulose for the purpose of improving the moldability.

Example 8

18.0 g of lactose (FlowLac90, MEGGLE JAPAN Co., LTD) and 2.0 g of hydroxypropylcellulose (HPC-SSL-SPP, NIPPON SODA CO., LTD.) were mixed to give a mixture. The resulting mixture was then subjected to tableting at a tablet compression force of 4 kN with the simple tableting machine (HANDTAB-100, ICHIHASHI-SEIKI Co., Ltd.) to thereby obtain an inner core tablet (a truly-flat tablet) having a diameter of 7.6 mm and a weight of 210 mg, wherein a small amount of calcium stearate (Taihei Chemical Industrial Co. Ltd.) had been applied in advance to the mortar inner surface, and the surfaces of the upper-pestle and the lower-pestle in the above tableting machine.

4.5 g of the particulate composition obtained in Example 1 was mixed with 0.5 g of sodium carmellose (CMC Daicel, Daicel FineChem Ltd.) to give the composition for the outer layer according to the present invention.

210 mg of the resulting inner core tablet and 40 mg of the composition for the outer layer were loaded to the simple tableting machine (HANDTAB-100, ICHIHASHI-SEIKI Co., Ltd.) and subjected to tableting at a tablet compression force of 12 kN to thereby obtain a nucleated tablet (a truly-flat tablet) having a diameter of 8.0 mm and a weight of 250 mg, wherein a small amount of calcium stearate (Taihei Chemical Industrial Co. Ltd.) had been applied in advance to the mortar inner surface, and the surfaces of the upper-pestle and the lower-pestle in the above tableting machine.

Example 9

A nucleated tablet (a truly-flat tablet) having a diameter of 8.0 nm and a weight of 250 mg was obtained by the same way as in Example 6 except that 4.5 g of the particulate composition obtained in Example 2 was mixed with 0.5 g of sodium carmellose (CMC Daicel, Daicel FineChem Ltd.) to give the composition for the outer layer according to the present invention.

Example 10

A nucleated tablet (a truly-flat tablet) having a diameter of 8.0 nm and a weight of 250 mg was obtained by the same way as in Example 8 except that 4.5 g of the particulate composition obtained in Example 4 was mixed with 0.5 g of sodium carmellose (CMC Daicel, Daicel FineChem Ltd.) to give the composition for the outer layer according to the present invention.

Comparative Example 5

A nucleated tablet (a truly-flat tablet) having a diameter of 8.0 mm and a weight of 250 mg was obtained by the same way as in Example 6 except that 4.5 g of erythritol (Erythritol T fine powder, Mitsubishi-Chemical Foods Corporation) was mixed with 0.5 g of sodium carmellose (CMC Daicel, Daicel FineChem Ltd.) to give the composition for the outer layer.

Example 11

17.9 g of lactose (FlowLac90, MEGGLE JAPAN Co., LTD), 2.0 g of hydroxypropylcellulose (HPC-SSL-SFP, NIPPON SODA CO., LTD.) and 0.1 g of calcium stearate (Taihei Chemical Industrial Co. Ltd.) were mixed to give a mixture. The resulting mixture was then subjected to tableting at a tablet compression force of 5 kN with the simple tableting machine (HANDTAB-100, ICHIHASHI-SEIKI Co., Ltd.) to thereby obtain an inner core tablet (R14 tablet) having a diameter of 10.0 mm and a weight of 400 mg.

4.5 g of the particulate composition obtained in Example 1 was mixed with 0.5 g of sodium carmellose (CMC Daicel, Daicel FineChem Ltd.) to give the composition for the outer layer according to the present invention.

400 mg of the resulting inner core tablet and 200 mg of the composition for the outer layer were loaded to the simple tableting machine (HANDTAB-100, ICHIHASHI-SEIKI Co., Ltd.) and subjected to tableting at a tablet compression force of 14 kN to thereby obtain a nucleated tablet (R14 tablet) having a diameter of 12.0 mm and a weight of 600 mg, wherein a small amount of calcium stearate (Taihei Chemical Industrial Co. Ltd.) had been applied in advance to the mortar inner surface, and the surfaces of the upper-pestle and the lower-pestle in the above tableting machine.

Example 12

A nucleated tablet (R14 tablet) having a diameter of 12.0 mm and a weight of 600 mg was obtained by the same way as in Example 11 except that 4.5 g of the particulate composition obtained in Example 2 was mixed with 0.5 g of sodium carmellose (CMC Daicel, Daicel FineChem Ltd.) to give the composition for the outer layer according to the present invention.

[Evaluation of Hardness, Easiness to Peel Off a Surface and Slipperiness]

Tablet Hardness, easiness to peel off a surface and slipperiness of each tablet produced in Examples 8-12 and Comparative Example 5 are shown in Table 3.

The results shown in Table 3 demonstrate that the nucleated tablets that were coated with the composition for the outer layer comprising the sugar alcohol granulated with spraying of the water-insoluble polymer (the particulate composition according to the present invention) and the water-soluble polymer in Examples 8-12 had such an excellent properties that easiness to peel off the surface was inhibited without deteriorating slipperiness, when compared to the tablet obtained by using the mixture of the sugar alcohol and the water-soluble polymer as the outer layer in Comparative Example 5.

Example 13

13.7 g of lactose (FlowLac90, MEGGLE JAPAN Co., LTD), 2.0 g of hydroxypropylcellulose (RPC-SSL-SFP, NIPPON SODA CO., LTD.), 4.0 g of vitamin C (Iwaki Seiyaku Co., Ltd.), 0.2 g of sucralose (Sucralose, San-Ei Gen F.F.I., Inc.) and 0.1 g of magnesium stearate (Taihei Chemical Industrial Co. Ltd.) were mixed to give a mixture. The resulting mixture was then subjected to tableting at a tablet compression force of 2 kN with the simple tableting machine (HANDTAB-100, ICHIHASHI-SEIKI Co., Ltd.) to thereby obtain an inner core tablet (R14 tablet) having a diameter of 10.0 mm and a weight of 400 mg.

9.0 g of the particulate composition obtained in Example 2 was mixed with 1.0 g of sodium carmellose (CMC Daicel, Daicel FineChem Ltd.) to give the composition for the outer layer according to the present invention.

400 mg of the resulting inner core tablet and 200 mg of the composition for the outer layer were loaded to the simple tableting machine (HANDTAB-100, ICHIHASHI-SEIKI Co., Ltd.) and subjected to tableting at a tablet compression force of 6 kN to thereby obtain a nucleated tablet (R14 tablet) having a diameter of 12.0 mm and a weight of 600 mg, wherein a small amount of calcium stearate (Taihei Chemical Industrial Co. Ltd.) had been applied in advance to the mortar inner surface, and the surfaces of the upper-pestle and the lower-pestle in the above tableting machine.

Example 14

A nucleated tablet (R14 tablet) having a diameter of 12.0 mm and a weight of 800 mg was obtained by the same way as in Example 13 except that the tableting was done using 400 mg of the composition for the outer layer

[Evaluation of Hardness, Thickness of the Outer Layer, Easiness to Peel Off a Surface, Slipperiness and Taste-Masking Effect]

Tablet Hardness, thickness of the outer layer, easiness to peel off a surface, slipperiness and taste-masking effect of each tablet produced in Examples 13 and 14 are shown in Table 4.

TABLE 3

|  | Ex. 8 | Ex. 9 | Ex. 10 | Ex. 11 | Ex. 12 | Comp. Ex. 5 |
|---|---|---|---|---|---|---|
| Tablet Compression Force (kN) | 12 | 12 | 12 | 12 | 14 | 12 |
| Tablet Hardness (N) | 103 | 100 | 182 | 108 | 99 | 127 |
| Easiness to peel off a surface (number) | 0 | 0 | 0 | 0 | 0 | 5 |
| Slipperiness | 3 | 3 | 3 | 3 | 3 | 3 |

TABLE 4

|  | Ex. 13 | Ex. 14 |
|---|---|---|
| Tablet Compression Force (kN) | 6 | 6 |
| Tablet Hardness (N) | 105 | 103 |
| Thickness of the outer layer (mm) | 0.5 | 1.0 |
| Easiness to peel off a surface (number) | 0 | 0 |
| Slipperiness | 3 | 4 |
| Taste-masking effect (seconds) | 38.6 | 62.4 |

The results shown in Table 4 demonstrate that the nucleated tablets that were coated with the composition for the outer layer comprising the sugar alcohol granulated with spraying of the water-insoluble polymer (the particulate composition according to the present invention) and the water-soluble polymer in Examples 13 and 14 had such an excellent properties that easiness to peel off a surface was inhibited without deteriorating slipperiness, and the taste of the core tablet was masked. It was also demonstrated that it was possible to control taste-masking time by changing the thickness of the outer layer.

Example 15

267 g of the particulate composition 1 obtained in Example 1, 30 g of sodium carmellose (CMC Daicel, Daicel FineChem Ltd.) and 3 g of calcium stearate (Taihei Chemical Industrial Co. Ltd.) were mixed to give formulation 1. The formulation 1 was charged, to a dry granulator (TF-LABO, Freund Corporation), and then pulverized to give gelated granule. The following properties of the resulting gelated granule were measured.

Moldability: Moldability of the granule was evaluated in accordance with three-stage criteria below:
3: possible to obtain granule with a sufficient strength
2: to be broken when touched with hands
1: impossible to granulate Slipperiness: Three men and women, respectively took the tablet without water, and slipperiness was evaluated in accordance with three-stage criteria below:
3: slippery and easy to swallow
2: slightly slippery but hard to swallow
1: hardly slippery and hard to swallow Adhesiveness: Three men and women, respectively took the tablet without water, and adhesiveness was evaluated in accordance with three-stage criteria below:
3: not adhered to the inner of an oral cavity
2: slightly adhered to the inner of an oral cavity
1: strongly adhesive to the inner of an oral cavity

TABLE 5

|  | Ex. 15 |
| --- | --- |
| Moldability | 3 |
| Slipperiness | 3 |
| Adhesiveness | 3 |

The results in Table 5 shows that the granule having excellent moldability, slipperiness and adhesiveness could be produced by using the sugar alcohol granulated with spraying of the water-insoluble polymer.

INDUSTRIAL APPLICABILITY

The present invention significantly contributes to research and development of the composition for the outer layer of the easy-to-take solid preparation and the like.

The invention claimed is:

1. A particulate composition comprising a plurality of granules, wherein each granule comprises a sugar alcohol and a water-insoluble polymer of micro-fibrillated cellulose, wherein the micro-fibrillated cellulose has an average fiber length of 0.01-2 mm, and an average fiber diameter of 0.001-1 µm, and wherein a mixing ratio of the sugar alcohol and water-insoluble polymer is in a range of from 99:1 to 80:20 by weight.

2. The particulate composition according to claim 1, wherein the sugar alcohol comprises one or more selected from the group consisting of erythritol, xylitol, mannitol, sorbitol, lactitol, isomalt and maltitol.

3. A composition for an easy-to-take solid preparation, which comprises the particulate composition according to claim 1, and a gelling agent that will show slipperiness when it is brought into contact with water.

4. The composition according to claim 3, wherein the gelling agent comprises at least one kind of a water-soluble polymer.

5. The composition according to claim 4, wherein the water-soluble polymer is selected from the group consisting of sodium carmellose, xanthan gum, sodium alginate, carrageenan and gelatin.

6. The composition according to claim 3, comprising sodium carmellose, erythritol or xylitol, and the micro-fibrillated cellulose.

7. The composition according to claim 3, which is used as an outer layer of the easy-to-take solid preparation.

8. A solid preparation comprising the particulate composition according to claim 1.

9. An easy-to-take solid preparation comprising the composition according to claim 3.

10. The easy-to-take solid preparation according to claim 9, which is in a form of granule for foods or pharmaceuticals.

11. An easy-to-take solid preparation for foods or pharmaceuticals, wherein an inner core is coated with the composition that is used as an outer layer according to claim 7.

12. A method for the production of the easy-to-take solid preparation according to claim 9, comprising only a step of compression-molding the composition in a dry process.

* * * * *